US011112383B2

United States Patent
Kuroki et al.

(10) Patent No.: US 11,112,383 B2
(45) Date of Patent: *Sep. 7, 2021

(54) ODOR DETECTION SYSTEM, ODOR IDENTIFICATION DEVICE, AND ODOR IDENTIFICATION METHOD

(71) Applicant: KABUSHIKIGAISHA AROMA BIT, INC., Tokyo (JP)

(72) Inventors: Shunichiro Kuroki, Tokyo (JP); Kenichi Hashizume, Gunma (JP)

(73) Assignee: KABUSHIKIGAISHA AROMA BIT, INC.

( * ) Notice: Subject to any disclaimer, the term of this patent is extended or adjusted under 35 U.S.C. 154(b) by 206 days.

This patent is subject to a terminal disclaimer.

(21) Appl. No.: 16/537,089

(22) Filed: Aug. 9, 2019

(65) Prior Publication Data

US 2019/0383772 A1    Dec. 19, 2019

Related U.S. Application Data

(63) Continuation of application No. 15/443,436, filed on Feb. 27, 2017, now Pat. No. 10,422,771, which is a
(Continued)

(51) Int. Cl.
*G01N 29/02* (2006.01)
*G01N 27/12* (2006.01)
(Continued)

(52) U.S. Cl.
CPC .............. *G01N 29/022* (2013.01); *G01N 5/02* (2013.01); *G01N 27/00* (2013.01); *G01N 27/12* (2013.01);
(Continued)

(58) Field of Classification Search
CPC ........... G01N 2291/0215; G01N 27/00; G01N 27/12; G01N 27/414; G01N 29/02;
(Continued)

(56) References Cited

U.S. PATENT DOCUMENTS

| 2003/0007146 | A1 | 1/2003 | Malczewski et al. |
| 2004/0179970 | A1 | 9/2004 | Matsubara et al. |
| 2006/0191319 | A1* | 8/2006 | Kurup ............. G01N 33/24 73/23.34 |

FOREIGN PATENT DOCUMENTS

| CN | 101470121 A | 7/2009 |
| EP | 1457772 A | 9/2004 |

(Continued)

OTHER PUBLICATIONS

Albert, et al., Optical Multibead Arrays for Simple and Complex Odor Discrimination, Analytical Chemistry, vol. 73, No. 11, dated Jun. 1, 2001, pp. 2501-2508.
(Continued)

*Primary Examiner* — Jennifer Wecker
(74) *Attorney, Agent, or Firm* — Bracewell LLP; Brad Y. Chin

(57) ABSTRACT

Embodiments provide an odor identification system including an operation array unit including at least two or more sensors which interact with odor causative substances included in an odor factor of a gas sample, a sensor data processing unit processing data obtained by interaction with the odor factor in the operation array unit, an odor factor information storing unit storing information of the odor factor and the interaction pattern information of the odor factor in advance, and a pattern identification unit identifying the odor factor on the basis of an interaction pattern while referring to the pattern processed by the sensor data processing unit and the information of the odor factor information storing unit, and collating the interaction pattern with the known odor information, wherein the odor of the object to be measured is contained.

13 Claims, 7 Drawing Sheets

Related U.S. Application Data continuation of application No. PCT/JP2014/073418, filed on Aug. 29, 2014.

(51) Int. Cl.
*G01N 27/00* (2006.01)
*G01N 33/00* (2006.01)
*G01N 27/414* (2006.01)
*G01N 5/02* (2006.01)

(52) U.S. Cl.
CPC ........... *G01N 27/414* (2013.01); *G01N 29/02* (2013.01); *G01N 33/0031* (2013.01); *G01N 33/0062* (2013.01); *G01N 2291/0215* (2013.01)

(58) Field of Classification Search
CPC ............. G01N 29/022; G01N 33/0031; G01N 33/0062; G01N 5/02
See application file for complete search history.

(56) References Cited

FOREIGN PATENT DOCUMENTS

| | | |
|---|---|---|
| EP | 2267421 A1 | 12/2010 |
| JP | H01244335 A | 9/1989 |
| JP | H0666701 A | 3/1994 |
| JP | 2004271482 A | 9/2004 |
| JP | 2009186485 A | 8/2009 |
| JP | 4737726 B2 | 8/2011 |
| JP | 2012-124601 A | 6/2012 |
| WO | 03004981 A2 | 1/2003 |

OTHER PUBLICATIONS

CN201480081522.7 Chinese Office Action dated Nov. 29, 2018; 36 pgs.
E-nose Instruments co., Ltd. homepage (http://e-nose.co.jp/product00.html).
EP14900972.2 Supplementary Search Report dated Dec. 22, 2017; 5pgs.
Tokyo Institute of Technology Laboratory Publication Landfall vol. 39, p. 19-22, Apr. 2000 (http://silvia.mn.ee.titech.ac.jp/system.html).
Tonosaki, "Nioi" to "Kaori" no Shoutai (Identity of "Odor" and "Scent"), p. 69, 1.6-10.
SCOPE Project (http://o.ed.kyushu-u.ac.jp/SCOPE/Welcome.html).
PCT/JP2014/073418 International Search Report dated Nov. 4, 2014; 2 pgs.

* cited by examiner

ODOR DETECTION SYSTEM, ODOR IDENTIFICATION DEVICE, AND ODOR IDENTIFICATION METHOD

CROSS-REFERENCE TO RELATED APPLICATION

This application is related to, and claims priority to, U.S. patent application Ser. No. 15/443,436, filed on Feb. 27, 2017, which is a continuation application of International Application No. PCT/JP2014/073,418, filed Aug. 29, 2014. The contents of this application is incorporated herein by reference in its entirety.

BACKGROUND

Field

Embodiments relate to an odor detection system, an odor identification device, and an odor identification method for patterning an odor itself and identifying the odor. Embodiments also relate to a sensor used in the system. Moreover, embodiments relate to a device used in the sensor.

Description of the Related Art

An odor is identified as odor information (sensory information) when various chemical substances simultaneously and compositively act on olfactory cells. Meanwhile, in sensing odor most are intended to detect and measure a specific gaseous chemical substance related to an odor from a chemical substance group constituting the odor (hereinafter, also referred to as odor factor).

A chemical sensor, such as an ammonia sensor, a hydrogen sulfide sensor, or the like, is often used where such sensors are designed to specify a chemical substance among chemical substances constituting an odor or to measure an individual odor causative substance, for example, an odor causative substance having a specific odor such as ammonia, mercaptan, aldehyde, hydrogen sulfide, or amine.

The sensor forms a surface state having a physical and chemical selectivity with respect to a specific molecule, and measures the specific substance by using a change in surface state when the specific molecule reacts with the surface or is adsorbed to the surface, or separates and then measures a specific odor causative substance by using a means for separating a chemical substance such as an adsorption column, for example, by using a chromatography method.

As a sensor system which can be used in separation and measurement of individual odor causative substances as described above, a sensor system in which a surface plasmon (SPR) generated by interaction of metal nano-particles with laser light is used in a detector portion, a sensor system using a field-effect transistor in which source, drain, and gate electrodes are provided on semiconductor silicon and a molecule selection film is formed on the gate and which uses adsorption of a substance to the surface, a surface acoustic wave sensor measuring and detecting a change in propagation velocity of a surface acoustic wave due to adsorption of a substance to the surface, or a QCM sensor using a variation in resonant frequency of a quartz oscillator according to the weight of a substance attached to the surface.

As a conventional odor sensor, generally, a thin film having substance selectivity is formed on the surface of a detector in the sensor system and a specific substance which causes the odor is detected by the thin film.

There is also a sensor using a change in carrier density according to oxidation-reduction reaction of oxygen on the surface of a metal-oxide semiconductor set to a high temperature. However, in this sensor, oxidation reaction of a reducing substance occurs on the surface, and thus the surface cannot be coated with a film or the like having substance selectivity and only reducing substances can be measured. Therefore, this sensor is only effective for limited odor substances such as ammonia and hydrogen sulfide.

Meanwhile, regarding a sensor using a quartz oscillator or the like, an array-type odor sensor is disclosed in which a plurality of quartz oscillators are provided (for example, see Japanese Patent No. JP 4737726 B2).

In this sensor, by providing the plurality of quartz oscillators to be arranged in a specific direction with respect to a substrate, a large amount of gas containing a substance to be detected can efficiently contact a sensor unit and thus detection efficiency is improved.

In non-patent literature, Tokyo Institute of Technology Laboratory Publication LANDFALL Vol. 39, p. 19-22, April 2000 (http://silvia.mn.ee.titech.ac.jp/system.html) ("TITL"), there is an attempt to specify an odor by performing multivariate analysis using a plurality of sensors. In this case, a sensor system to be used is configured by a combination of monofunctional sensors that measure a specific chemical substance defined in advance. Thus, when a substance constituting the odor is already known, the odor can be expressed by multivariate analysis.

Recently, there is also an attempt that, when a plurality of luminescent molecules each responding to molecules having different polarities are applied onto a substrate and then exposed to an odor factor in order to detect and evaluate an odor itself as well as to detect and measure a specific substance constituting an odor as described above, the substrate emits light in a specific pattern in response to the odor, and then this pattern is captured and recorded to image the odor (for example, see SCOPE Project (http://o.ed.kyushu-u.ac.jp/SCOPE/Welcome.html) ("Scope Project").

In this odor imaging system, a multiple probe film is used in which particles obtained by combining compounds each identify a plurality of odors, for example, fluorescent nanoparticles for detection are arranged.

With such a configuration, when particles each are bonded with specific odor factors, the particles emit light and the light-emitting particles can be visualized by capturing them with a CCD camera or the like.

However, the aforementioned conventional sensor can only detect, for example, information related to substances having specific molecular structures on the basis of existence or level of an electrical resistance value or combination of prescribed substances and can only define odor causative substances (molecules) specified by the molecular structures, molecular weights and the like of the substances. Thus, even though the presence or absence of the substances can be detected, it is difficult to detect and identify odor information obtained by using olfactory sense of human beings such as an olfactory test as measurement results.

Non-patent literature, e-nose Instruments co., Ltd. homepage http://e-nose.co.jp/product00.html, also discloses an odor sensor, however, only detection and quantitative determination of a specific molecule can practically be performed by the level of oscillation frequency corresponding to the specific molecule.

In multivariate analysis disclosed in TITL, it is necessary to prescribe in advance the substance to be measured by each individual sensor used as sensors, and thus an odor configured by a substance which is not assumed by each sensor cannot be accurately expressed.

That is, since an odor has generally a complicated configuration formed from a plurality of chemical substances, there is a problem in that it is difficult to acquire or express odor information only by combination of mono-functional sensors each defining a specific object to be measured which is included in a certain odor.

In order to solve such a problem, in the method of SCOPE Project described above, light emitted from a fluorescent substance is captured. However, an excitation light source, CCD camera and the like are necessary for light emission is needed. Thus, in this case, a device itself would be larger and it is difficult to easily define and identify an odor.

SUMMARY

Embodiments have been made in view of the above-described problems.

Embodiments provide an odor detection system, an odor identification device, and an odor identification method which are capable of easily detecting, discriminating, and identifying an odor causative substance as a specific odor even in a mixed state of an unspecified number of odor causative substances.

According to at least one embodiment, there is provided an odor detection system which solves the above-described problems.

According to at least one embodiment, there is provided an odor detection system including an operation array unit (hereinafter also referred to as a "sensor array unit") including at least two or more sensors configured to interact with at least one or more odor causative substance groups included in an odor factor of an object to be measured, and a sensor data processing unit configured to process a result of the interaction obtained from the operation array as odor pattern information. The odor detection system further includes an odor factor information storing unit configured to store odor information including known odor factor information and known odor substance pattern information, and a pattern identification unit configured to identify an odor by referring to the odor pattern information processed by the sensor data processing unit and the information of the odor factor information storing unit, and further configured to collate the interaction pattern with the known odor information, wherein the odor of the object to be measured is contained.

According to at least one embodiment, the at least two or more sensors are a quartz oscillator sensor.

According to at least one embodiment, the at least two or more sensors are a surface acoustic wave sensor.

According to at least one embodiment, the at least two or more sensors are a field-effect transistor sensor.

According to at least one embodiment, the at least two or more sensors are a charge-coupled device sensor.

According to at least one embodiment, the at least two or more sensors are an organic conductive polymer sensor.

According to at least one embodiment, an arrangement of the at least two or more sensors can be changed.

According to at least one embodiment, the odor detection system further includes a sensor information unit configured to store arrangement information of the at least two or more sensors.

According to at least one embodiment, the odor detection system further includes a sample acquisition unit configured to acquire a sample including a measurement target.

According to another embodiment, there is provided an odor identification method, including providing interaction of a sensor array including at least two sensors with a sample, processing interaction information of the interacted sensors as sensor data, collating the interaction information processed as the sensor data with odor factor information, and identifying an odor by the collating.

According to at least one embodiment, the at least two sensors are one selected from a quartz oscillator sensor, a surface acoustic wave sensor, a field-effect transistor sensor, a charge-coupled device sensor and an organic conductive polymer sensor.

According to at least one embodiment, an arrangement of the at least two sensors can be changed.

According to another embodiment, there is provided an odor identification device, including a sensor comprising at least two sensors which are configured to sense a measurement target, a sensor data processing unit configured to process reaction data of the sensor, and a pattern identification unit configured to identify a measurement target on the basis of a sensor data pattern prepared by the processing of the sensor data.

According to at least one embodiment, the at least two sensors are one selected from a quartz oscillator sensor, a surface acoustic wave sensor, a field-effect transistor sensor, a charge-coupled device sensor and an organic conductive polymer sensor.

According to at least one embodiment, an arrangement of the at least two sensors can be changed.

According to another embodiment, there is provided an odor detection system including a sample acquisition unit configured to acquire a sample including a measurement target, and an reaction array unit including at least two or more sensors which interact with each odor factor in the sample and arrangement of which is changeable, a sensor data processing unit configured to process a pattern obtained by interaction with the odor factor in the reaction array unit. The odor detection system further includes an odor factor information storing unit configured to store information of the odor factor and interaction pattern information of the odor factor in advance; a sensor arrangement information unit storage sensor configured to store sensor arrangement information of the reaction array unit; and a pattern identification unit configured to identify the odor factor on the basis of an interaction pattern while referring to data processed by the sensor data processing unit, the information of the odor factor information storing unit, and the information of the sensor arrangement information unit.

According to another embodiment, there is provided a program causing a computer to function as an odor detection system including a sample acquisition unit acquiring a sample including a measurement target, a reaction array unit including at least two or more sensors which interact with each odor factor in the sample and arrangement of which is changeable, a sensor data processing unit processing data obtained by interaction with the odor factor in the reaction array unit, an odor factor information storage unit storing information of the odor factor and interaction pattern information of the odor factor in advance, a sensor arrangement information unit storing sensor arrangement information of the reaction array unit, and a pattern identification unit identifying the odor on the basis of an interaction pattern while referring to the data processed by the sensor data processing unit, the information of the odor factor information storing unit, and the information of the sensor arrangement information unit.

By using the system according to various embodiments, it is possible to detect a specific "odor" in an environment where a plurality of substances are actually mixed which is conventionally difficult to detect and identify. Accordingly, it is possible to detect, identify, and express a specific odor configured by an unspecified substance group (being not limited to a specific substance constituting the odor), which is conventionally difficult to detect, identify, and express.

DETAILED DESCRIPTION

Figure 1:
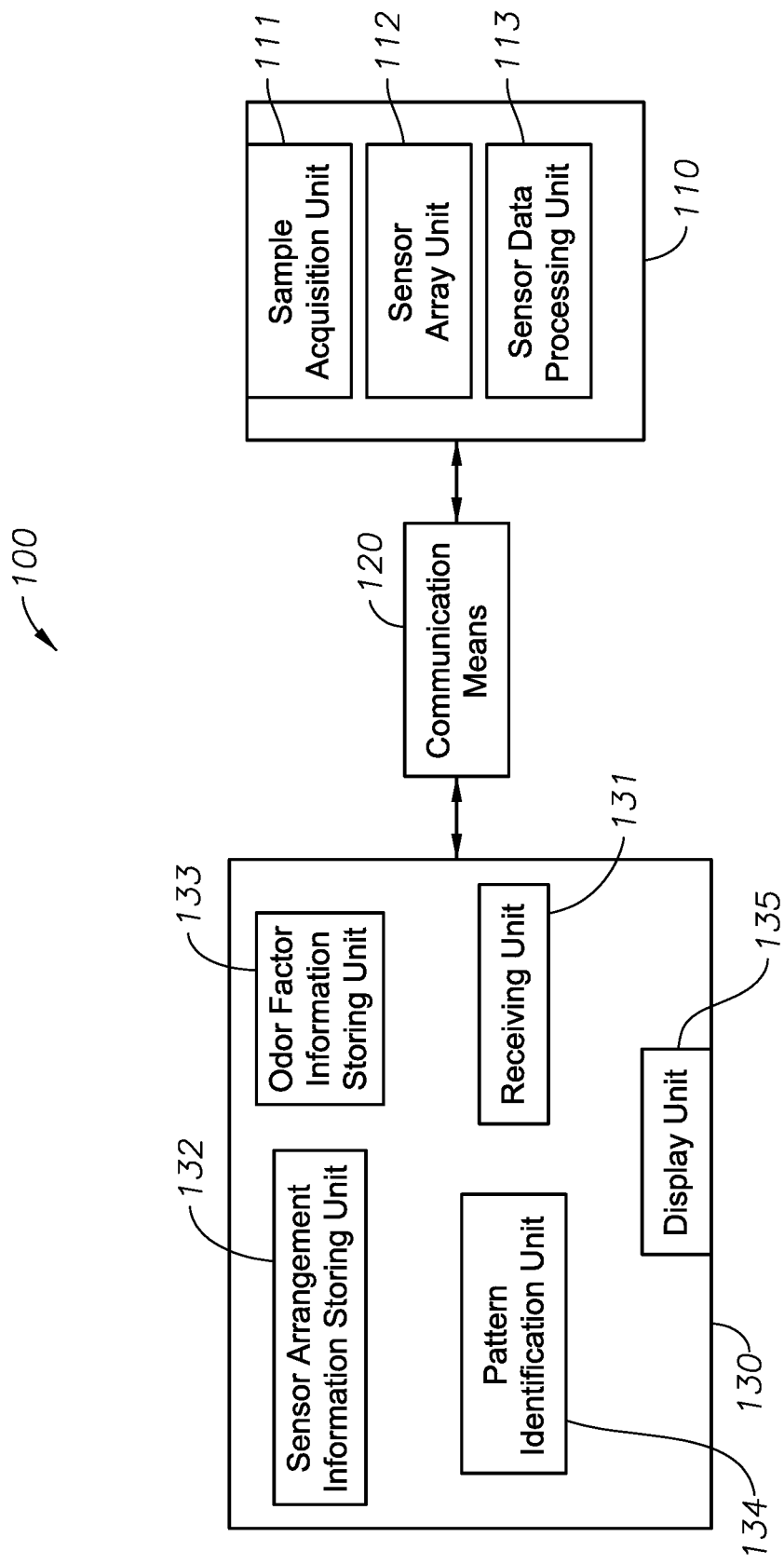
FIG. 1 is a schematic diagram of an odor detection system according to an embodiment.

Hereinafter, various embodiments of the odor detection system and method are described.

Odor Detection System

According to at least one embodiment, there is provided an odor detection system including an operation array unit including at least two or more sensors, which interact with an odor sample, that is, an odor factor in the air at a specific place; a sensor data processing unit processing a pattern obtained by reaction of an odor causative substance in the operation array unit; an odor factor information storing unit storing information of the odor and operation pattern information of the odor in advance; and a pattern identification unit identifying an odor by referring to the odor pattern information processed by the sensor data processing unit and the information of the odor factor information storing unit, and collating the interaction pattern with the known odor information, wherein the odor of the object to be measured is contained.

Herein, an "odor" includes a collection of specific single molecules or molecular groups consisting of different molecules each at different concentrations and which can be acquired as olfactory information by human beings or living beings including human beings.

An "odor causative substance" means specific molecule(s) or compound(s) constituting an odor.

An "odor factor" indicates a substance group including a plurality of odor causative substances and having a specific configuration of the odor.

In general, olfactory mechanism of noses of animals including humans may be described as follows.

First, when an odor factor is input from the nose, an odor causative substance penetrates in a specific mucous membrane called olfactory epithelium of the top portion of the nasal cavity, and is then sensed. Then, olfactory cells in the olfactory epithelium generate electric signals, the electric signals are transmitted to the olfactory nerve, the olfactory bulb, and the brain (limbic cortex), and thus the sense of odor is generated.

Herein, olfactory receptors (odor sensors) to catch an odor are present in olfactory cilia widespread in the mucosal layer of the olfactory epithelium. Some of the olfactory receptors react with one odor causative substance included in the odor factor to detect the odor. Further, when the concentration of the odor varies, the combination of olfactory receptors to react varies so that the odor is sensed as a different odor.

Amoore has focused on that a plurality of odor causative substances each having a different molecular structure provide similar odors, found out that some of the outer shapes of the molecules providing similar odors are significantly similar to one another, and proposed that there is a possibility that the olfactory receptors identify the shape structure of molecules.

In "Nioi" to "Kaori" no Shoutai (Identity of "Odor" and "Scent")' written by Keiichi TONOSAKI, it is described that the olfactory receptors identify oscillation frequencies provided by respective odor causative substances.

As described above, for easy explanation, it is considered that the olfactory receptors do not detect relatively direct information, by which a compound can be identified and which is hitherto used for chemical analysis, such as molecular weight, oxidation-reduction potential, or binding position with a functional group, among attributes of odor causative substances but detect indirect properties of substances such as outer shape information of molecules.

In the system according to various embodiments, when the operation array unit including a plurality of sensors as described above acts like an olfactory receptor, the odor itself including a plurality of odor causative substances can be identified by detection of various odors and their level of concentration.

Therefore, the system according to various embodiments is a sensor, which simulates how an "odor" interacts with the nose and is detected as specific information, and has a different principle from those of the conventional arts in which the "odor" is specified by individually specifying each "odor causative substances."

1a. Odor Detection System

Hereinafter, embodiments are described using the drawings.

FIG. 1 is a block diagram of an odor identification system according to an embodiment.

An odor identification system 100 according to an embodiment includes a sample information acquisition unit 110, a communication means 120, and an information processing unit 130.

According to at least one embodiment, the sample information acquisition unit 110 provided to obtain information of an odor sample is provided with a sample acquisition unit 111 acquiring an odor sample, a sensor array unit 112 including at least two sensors to interact with substances of the acquired sample, and a sensor data processing unit 113 processing the sensor data of the sample substance and of the interaction state in the sensor array unit 112.

According to at least one embodiment, the communication means 120 is connected to the sample information acquisition unit 110 and the information processing unit 130. For example, direct connection, RS-232, USB or a means for establishing various networks such as LAN with or without wire and Wi-Fi can be appropriately used.

According to at least one embodiment, the information processing unit 130 is provided with, for example, a data receiving unit 131 acquiring a sample for identification and receiving the data, an odor factor information storing unit 133 storing odor information related to an odor factor in advance in order to refer to the received data, a sensor arrangement information storing unit 132 storing information related to the sensor array unit 112 disposed in the system in order to similarly refer to the data of the odor factor, a pattern identification unit 134, wherein the registering identification information patterns of information of a sample serving as a measurement target in the sensor array unit 112 are registered in advance and wherein the identification information patterns when the sample is measured are referred to, and a display unit 135 displaying measurement data obtained by referring to information of each unit of the system and the sample.

According to at least one embodiment, the sensors to be disposed in the sensor array unit 112 can be selected depending on a substance to be measured. That is, a sensor having a specific property with respect to the odor causative substance to be detected and identified can be appropriately selected and disposed.

According to at least one embodiment, the number of sensors to be disposed is at least two, and thus each of the plurality of odor causative substances included in the odor factor can be specifically detected.

According to at least one embodiment, the concentration or the like of the odor causative substance as a measurement target can be measured, for example, by changing the detection sensitivity in each sensor.

With such a configuration, various odor causative substances present in a gas can be measured as samples. Moreover, conventionally, only the intensity of odors specific to the molecules can be measured from the amount of each molecule included in the odor factor; however, with such a configuration according to various embodiments, it is possible to discriminate and identify the odor factor measured for a combination of detection patterns of the sensors as a tangible odor, that is, a complex of the plurality of odor causative substances.

According to at least one embodiment, the odor detection system is further provided with the communication means 120 used for transmitting sample information data obtained by the sample information acquisition unit 110 to the information processing unit 130.

That is, the information concerning the sample substance which has been acquired by the sample information acquisition unit 110, operated, and processed as sensor data is transmitted to the information processing unit 130 through the communication means 120. Referring to the sensor data processed patterns and the odor factor information storing unit 112 or referring to the sensor data processed patterns and the information of both of the odor factor information storing unit 133 and the sensor arrangement information storing unit 132, in the server of the system a specific odor of the odor factor which is the measurement target can be detected and identified based on the display patterns detected by the sensors of the sensor array unit 112.

1b. Sensor Array

The sensor array unit 112 of the system 100 according to an embodiment is provided with at least two odor sensors. The number of sensors to be disposed is not particularly limited, but a configuration in which two or more sensors are disposed may be employed.

Most of so-called odor sensors conventionally used have one probe for detecting odor causative substance molecule, and in such case, only qualitative or quantitative measurement of the single odor causative substance molecule can be performed.

On the other hand, the sensor array unit 112 of the system 100 according to an embodiment is provided with a plurality of sensors. Each sensor can be configured to show a specific reaction with respect to the molecule(s) to be operated and can adjust the operation degree to each target molecule(s).

With such a configuration, a user of the odor detection system according to an embodiment may dispose only the number of sensors necessary for detecting the desired number of substances to be detected and identified. Thus, the plurality of odor causative substances included in the odor factor can be qualitatively or quantitatively measured and the odor factor can be identified as a whole.

That is, in the sensor array of the sensor array unit 112 according to an embodiment, the number and the arrangement of sensors specifically operating with respect to specific substance molecules and types of sensors can be determined after the reaction patterns in the entire array at the time of operation are arbitrary designed. When the reaction patterns are stored in advance in the sensor arrangement information storing unit 132 provided in the information processing unit 130, the reaction patterns can be collated with the reaction in the sensor array unit 112 with respect to each odor factor. Therefore, a collection of the plurality of odor causative substances can be identified, and identification of the odor factor including the plurality of odor causative substances that cannot be substantiated by the conventional odor sensor can be accordingly performed.

According to at least one embodiment, the sensor used herein is not particularly limited, and various sensors can be appropriately used depending on the purpose or the like of the occasion.

Examples of the sensor include an electrochemical sensor, a MOS field-effect transistor sensor, a metal-oxide-semiconductor sensor, an organic conductive polymer sensor, a quartz oscillator sensor (QCM sensor), a surface acoustic wave sensor, and a charge-coupled device sensor, as non-limiting examples.

Among these sensors, for example, a quartz oscillator sensor is suitably used.

Figure 2:
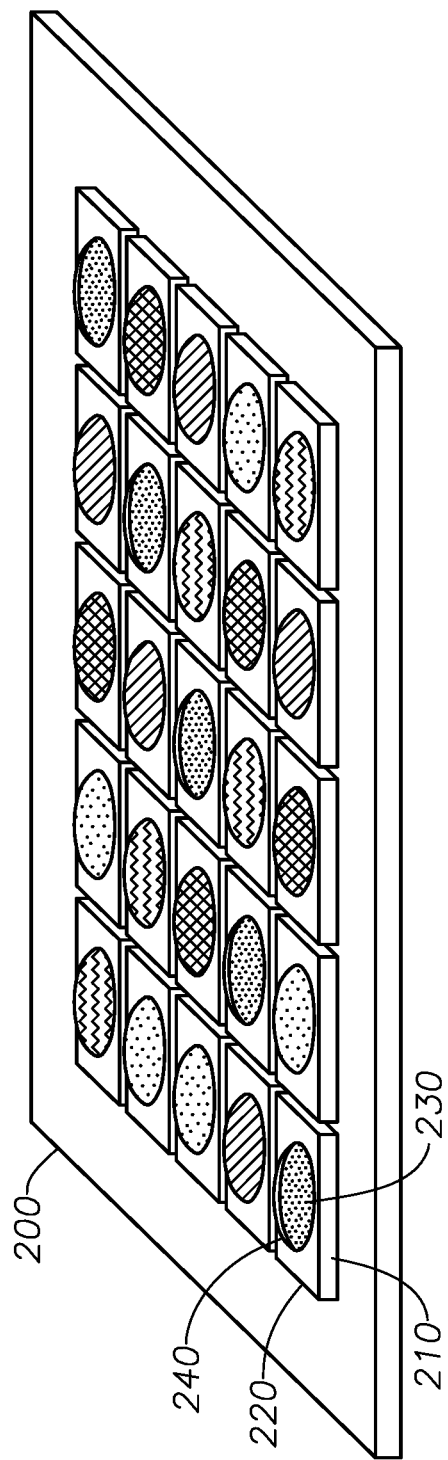
FIG. 2 is an outline diagram of a sensor array, which is used in the odor detection system according to an embodiment.

FIG. 2 is a plan perspective view of a sensor array 200 using a quartz oscillator element (QCM element) 210 as an example of a usable sensor according to an embodiment.

The QCM-type sensor multi array 200 according to an embodiment is formed by mounting a plurality of QCM elements 210 configured by a quartz substrate 220, an oscillating unit 230, a functional film 240 provided on the surface of the oscillating unit, and an excitation electrode (not illustrated) exciting oscillation, and is a multi-array QCM sensor in which one or more QCM elements 210 each having different functional film 240 are mounted on the common substrate 200.

Figure 3:
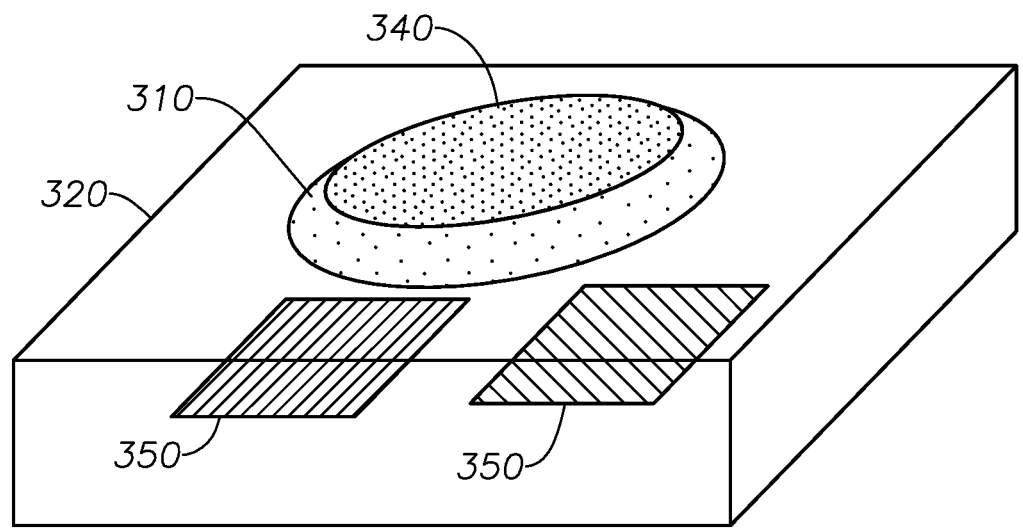
FIG. 3 is a perspective view of a quartz oscillator, which is used in the sensor array used in the odor detection system according to an embodiment.
Figure 4:
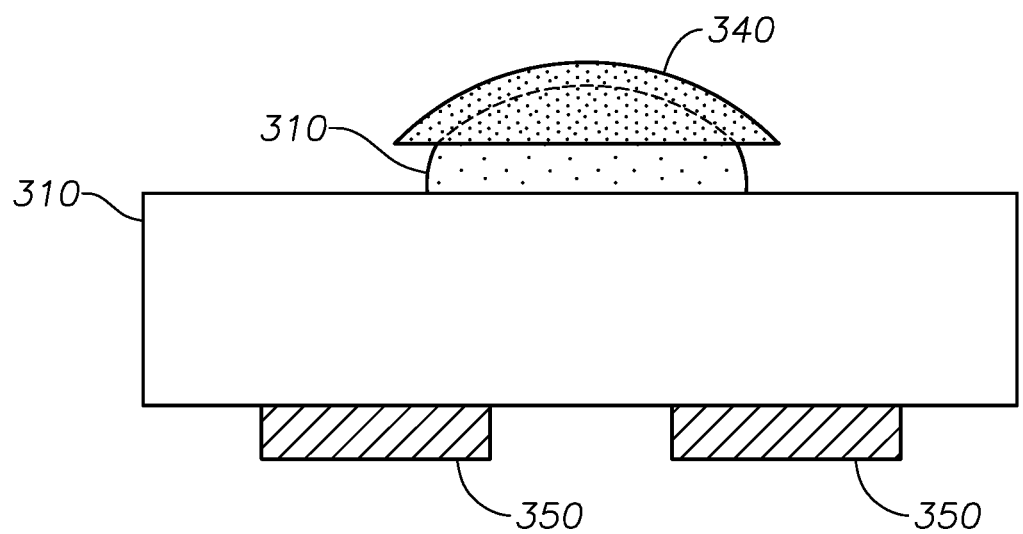
FIG. 4 is a cross-sectional view of the quartz oscillator, which is used in the sensor array used in the odor detection system according to an embodiment.

FIG. 3 is a perspective view of a QCM element and FIG. 4 is a cross-sectional view of the element according to various embodiments.

1c. QCM Element

It is well known that the quartz oscillator, that is, the QCM element is configured as a mass sensor that detects a change in weight on the electrode surface as a change in frequency. In general, as illustrated in FIG. 3, the QCM element has a configuration in which an electrode and a functional film 340 absorbing a gas or an odor molecule is disposed on one surface of a quartz substrate 320 and excitation electrodes 350 are disposed on the other surface thereof.

When a QCM element 310 is oscillated and driven by the excitation electrodes 350 and an odor molecule as a substance to be measured reaches the functional film 340, which is in contact with external air on the surface of the QCM element 310, the resonant frequency of the QCM element 310 is changed by adsorption and interaction of the odor molecule. The change in frequency is electrically specified.

There are various types of chemical sensors conventionally used. In particular, considering QCM, that is, a physical oscillation detecting element such as a quartz oscillator, when a device is decreased in size, that is, the thickness and the electrode area of the device are decreased, the resonant frequency or the like of the quartz oscillator is increased, and as a result, a frequency change rate is increased, so that the detection limit is decreased. Accordingly, the QCM element is characterized to detect a chemical substance with low concentration.

By arbitrarily mounting and disposing the plurality of QCM elements each having a different functional film on the common substrate, the multi-array QCM type sensor system according to an embodiment as illustrated in FIG. 2 is obtained. The excitation electrode of each QCM element is wired in a frequency counter or the like and electrically specifies a change in frequency of each QCM element as described above.

The QCM elements each coated with a different functional film show different interactions to the odor causative substances as measurement targets. By disposing the sensors each provided with a different functional film on the array, changes in frequency of each QCM element are detected and analyzed so that the odor factor can be qualitatively or quantitatively analyzed.

For example, more specifically, it can be obtained arrangement information of the sensors such as which odor substance the sensor adsorbs or detects as information in an X-axis direction and Y-axis direction in the arrangement rule of each QCM element, and it can be obtained qualitative odor patterns formed of at least three-dimension for changes in frequency (adsorption property or degree of interaction) of the QCM element group.

Herein, the QCM element 310 and the excitation electrode 350 can be formed by an arbitrary conductive material.

For example, inorganic materials, such as gold, silver, platinum, chromium, titanium, aluminum, nickel, nickel-based alloy, silicon, carbon, and carbon nanotube, and organic materials such as conductive polymers (for example, polypyrrole, polyaniline and the like) can be mentioned.

For example, by using an inclined functional film in which the intensity of hydrophobicity, hydrophilicity, or the like is slightly inclined in the spatial axis direction by concentration distribution or chemical modification, each sensor configuring each array can interact with odor causative substance(s) as substance to be measured in a slightly different way.

In addition, by changing the resonant frequency of each oscillator, the influence caused from other coexisting oscillators, that is, crosstalk can also be decreased, which is preferable. Each oscillator in the common substrate can be arbitrarily designed to show a different sensitivity.

When the resonant frequencies of respective quartz oscillators are the same, there is also an attempt to change the resonant frequency by changing the thickness of the odor adsorption film. In addition, elements each having a different resonant frequency (for example, an overtone mode in which the thickness of the quartz substrate is changed) can also be used.

Regarding the type of the common substrate, a silicon substrate, a substrate formed from quartz crystal, a printed circuit board, a ceramic substrate, a resin substrate, or the like can be used.

The quartz substrate 320 is a multi-layer wiring substrate, such as an interposer substrate. In the quartz substrate, an excitation electrode 350 for exciting the quartz substrate, mounting wirings, and an electrode (not shown) for passing current are disposed at arbitrary positions, and the quartz substrate is connected, for example, to a bump as shown in FIGS. 3 and 4 for electronic grounding or conduction to another electronic circuit board or the like.

As an example of the shape of the quartz oscillator, a convex shape is more preferable from the viewpoints that the convex shape is small, and energy is blocked in the oscillator, interference between respective oscillators in the substrate is prevented, and improvement in a Q value is expected when the convex shape is used.

As the convex shape providing the thickness distribution to the quartz oscillator (a lens shape or a emboss shape), it can be employed a structure in which a separate-type excitation electrode (an electrode inputting a voltage for oscillating) is configured as one surface and a conductive film is disposed at a position opposite to the surface facing the excitation electrode.

It is known that a combining with another oscillation mode is accordingly suppressed and interference such as propagation or reflection between the quartz oscillators at the time of multi-arraying in the oscillator can be prevented. Therefore, as the size and the capacity are decreased, the distance between the oscillators is shortened and thus effect is increased.

Similarly, by the oscillation energy containment effect, the Q value and conductance can be increased and a quartz oscillator, in which the oscillation energy is not lowered even when the size thereof is decreased and which is less likely to be interfered from external contact. As a result, an S/N ratio is improved to achieve high sensitivity.

Incidentally, when the QCM sensor to be formed herein has a structure called a reverse mesa shape or a convex shape, surface mounting in proximity can be implemented, and thus such a structure is suitable for miniaturization. In the present example, a convex shape more suitable for miniaturization is mentioned as an example; however, if there is a more optimal shape, such a shape can be selected.

There is also an attempt to use a convex hybrid shape in which a convex shape is put into the recess of the reverse mesa shape. Also, in the case of an elliptical shape as well as a circular shape, improvement in sensitivity (Q value) of the QCM element, or the like is exhibited. As the shape of the quartz oscillator, a more optimal shape may be used in consideration of cost or the like.

Hereinbefore, regarding the configuration of the sensor array according to an embodiment, the sensor array using a quartz oscillator has been described as an example; however, needless to say, the various embodiments are not limited thereto.

2. Odor Identification Method

Next, an odor identification method according to various embodiments will be described.

2a. Outline of Odor Identification Method

Figure 5:
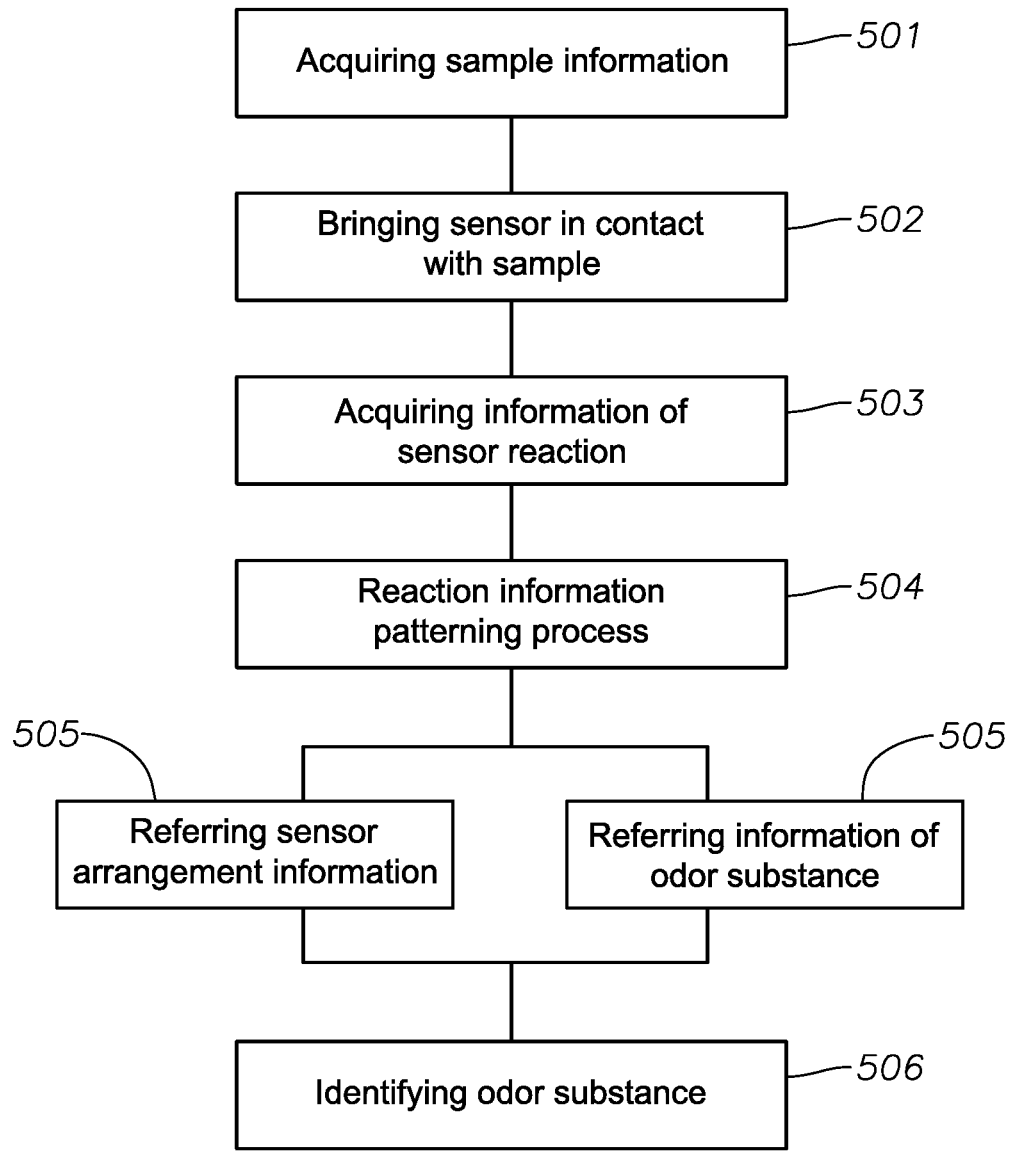
FIG. 5 is a flowchart illustrating a procedure of the odor detection system according to an embodiment.

FIG. 5 is a flowchart illustrating an outline of an odor identification method according to an embodiment.

First, the sample information acquisition unit 110 of the odor identification system 100 according to an embodiment, as illustrated in FIG. 1, is brought into contact with an odor factor which is to be a measurement target (Step 501). Molecules of the odor factor are introduced through the sample acquisition unit 111 by this contact and then sent to the sensor array unit 112 (Step 502).

According to at least one embodiment, the sensor array unit 112 has a multi-array structure in which at least two or more sensors are disposed. Herein, each sensor is configured to interact with each odor causative substance as target at a specific degree and to interact with various odor causative substances included in the odor factor. Gas containing the introduced odor factor is brought into contact with the array portion to acquire the result of interaction by each sensor as data (Step 503).

The interaction data is, for example, fluorescence response, a change in electrical resistance, or a change in oscillation frequency which varies depending on the sensor to be used.

The patterns of the interaction data are associated with a specific odor factor to be measured, and then sensor data is processed as position information of sensors reacting on the sensor array and information including the degree of the interaction (Step 504).

Next, the interaction pattern information processed as the sensor data is sent to the information processing unit 130, data in the sensor arrangement information storing unit 132 and the odor factor information storing unit 133 are referred to (Step 505), the corresponding patterns are read out, and then the odor factor is identified (Step 506).

Herein, when a single odor causative substance is desired to be detected, the odor causative substance can also be specified by referring to and only collating the odor causative substance information without referring to the sensor arrangement information.

2b. Specific Example

Next, the flow of the identification method will be described in detail with reference to the flow of FIG. 5, FIG. 6, and FIG. 7.

Figure 6:
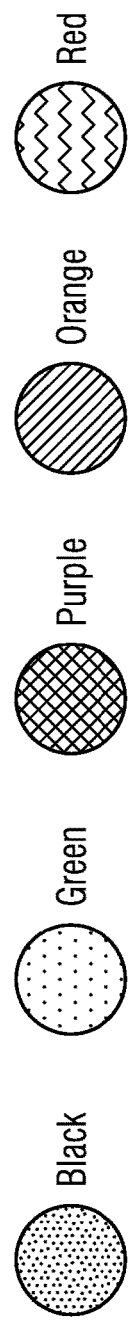
FIG. 6 is a schematic diagram illustrating interaction of an odor causative substance with the sensor array used in the odor detection system according to an embodiment and arrangement information of the sensor array.

FIG. 6 is a schematic diagram illustrating interaction of an odor causative substance with the sensor array and arrangement information of the sensor array according to an embodiment.

Figure 7:
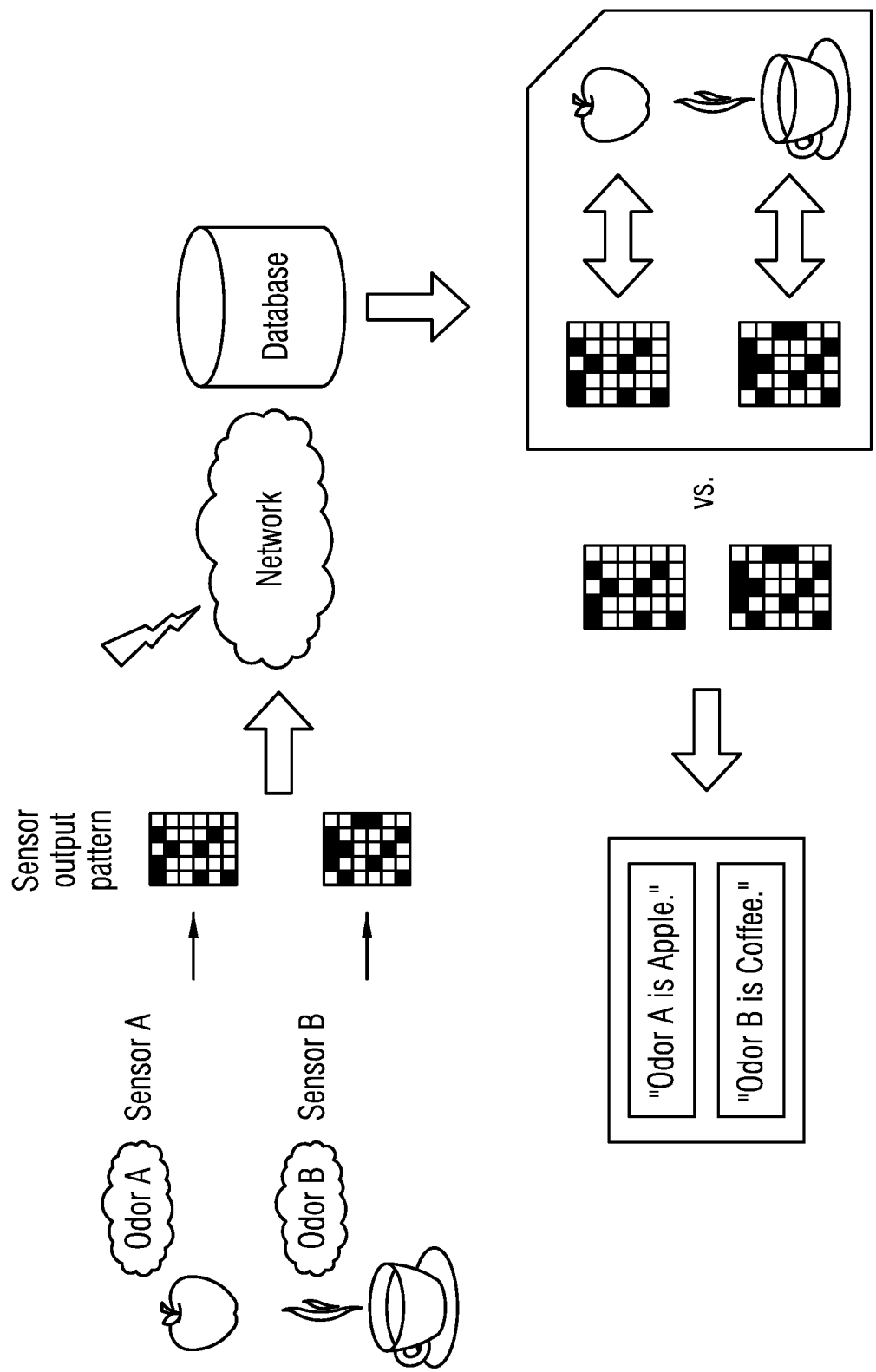
FIG. 7 is a system outline diagram illustrating processes of detecting and identifying odors of apple and coffee as an example of using the odor detection system according to an embodiment.

FIG. 7 is a system outline diagram illustrating processes of detecting and identifying odors of an apple and coffee as an example.

In this example, the odor factor can be detected and identified by only the information of the odor causative substance; however, by referring to both the odor factor information and the sensor information as described above, for example, by referring to both sensor-related information in which arrangement information of sensor parts, sensor configuration information, sensor product information, or the like is registered in advance and the odor factor information, data processing can be performed as a specific pattern in the case of using the sensor.

With such a configuration, the information of the odor factor to be measured can be correlated with personal information or the like of a user using the sensor. For example, the related information can be applied to security techniques such as personal authentication or the like, or can be used for diagnostic techniques in the medical field, and thus the use application of the odor factor information can be broadened.

First, the user causes the sensor to specify a specific odor factor as a measurement target with the odor identification system according to an embodiment. In this example, the measurement targets are odors of apple and coffee which are designated as Odor A and Odor B, respectively. These odors are stored as the odor factors in the odor factor information storing unit.

First, a sample including odor factors of apple and coffee is brought into contact with the present system to acquire the sample (Step 501). The gas of the acquired sample is sent to a sensor array unit 600 of FIG. 6 and reaction occurs in the array unit.

Herein, QCM element groups 601, which are mounted on the sensor system according to an embodiment and each are coated with a different functional film, interact in a different way against a plurality of odor causative substances included in apple or coffee, and each QCM element outputs frequency change according to each reaction.

That is, in a certain element group 601, the element group of (X1, Yn) strongly interacts, for example, with the apple odor component, that is, amyl acetate as an odor substance, and the degree of the interaction decreases as n of Yn increases. Meanwhile, the element group of (Xn, Y1) is configured to have a functional film which strongly interacts with hexyl acetate or the like, and the degree of the interaction decreases as n of Xn increases.

The element group of (X2, Yn), the element group of (X3, Yn), and the element group of (X4, Yn) each are configured to have functional films which relatively strongly interact with caffeine as coffee odor components, theophylline, and theobromine, respectively.

These configurations (position information and functional film information) and sensor product information (production number of the sensor, array position information (X, Y), type of each QCM element, and the like) are stored in advance in the sensor arrangement information storing unit 132 illustrated in FIG. 1.

With such a configuration, each element 601 can detect as a pattern the change in oscillation frequency of the QCM element, which is correlated with element arrangement, according to the concentration of the odor component.

The change in frequency of each element generated by the interaction between the odor substance of the sample and each element is converted into digital data, the digital data is sent to the sensor data processing unit 113, and then the digital data is processed as sensor data by the sensor data processing unit 113 to be converted, for example, into image data, thereby acquiring sensor array information (Step 504).

At this time, the pattern output as sensor data by using general sensor data processing is compared with information of database. For example, as a general sensor data processing technique, a two-dimensional barcode reader or an approximation information processing technique such as face recognition or fingerprint authentication can be used.

In this way, when there is interaction in each element 601 illustrated in FIG. 6, outputs corresponding to the intensity of interaction of the functional film of each sensor is made from each element 601, and at the same time, arrangement information of each element 601 is output.

At this time, for example, an electronic device having the system according to an embodiment mounted therein can calculate an odor pattern (X, Y, or QCM output) by referring to product information of the sensor elements (such as production number of sensors, array position information (X, Y), or type of each QCM element), which is stored in advance in the sensor arrangement information storing unit via the network, on the network and collating the product information with output data of a change in frequency of each QCM element. That is, a matrix pattern of the array as illustrated in FIG. 7 is obtained.

Thereafter, in Step 505, by collating the interaction pattern data with the data of the odor substance information storing unit and the sensor arrangement information storing unit, which stores properties and arrangement of the sensor array unit, information of sensors as products, and by referring to those data, the odor factor included in the sample is specified (Step 506).

Then, as illustrated in FIG. 7, when the output pattern approximates an odor pattern of apple or coffee or corresponds to the odor pattern thereof, the result "Odor A is an odor similar to an apple" or "Odor B is an odor similar to coffee" is returned to the user.

As described above, when the odor detection system according to an embodiment acquires the interaction patterns between the previously stored arrangement rule information of the QCM elements of the sensor system and the odor factors obtained from output information, and at the same time, refers to the database which is constructed on the network and in which the odor factor information is stored an odor can be easily identified in the cloud environment in the case of a user device on which the sensor system according to an embodiment is mounted.

As a matter of course, the user can arbitrarily register an odor target substance together with an odor pattern in the database. Thus, a more secure and safe system can be designed.

3. Odor Identification Device

The odor identification device according to an embodiment has a configuration for carrying out the odor detection system and the method therefor described above.

That is, the odor identification device includes a sensor unit including at least two sensors sensing a measurement target; a sensor data processing unit processing reaction data of the sensor unit; and a pattern identification unit identifying the measurement target on the basis of a sensor data pattern prepared by the sensor data processing.

According to at least one embodiment, the sensor unit and the pattern identification unit correspond to the sample information unit 110 and the integrated system unit 130, respectively, and each unit may be provided in one device or may be configured as individual devices. Examples thereof will be described below.

4. Utilization Example of System

4a. Portable Device Provided with Odor Detection System

The system according to an embodiment can minimize the sensor array unit, and thus the sample information acquisition unit can also be incorporated in a portable device such as a smartphone. In such case, the information processing unit may also be incorporated in the device or may be configured to refer to information necessary for the information processing unit provided outside the device via a network communication means.

Figure 8:
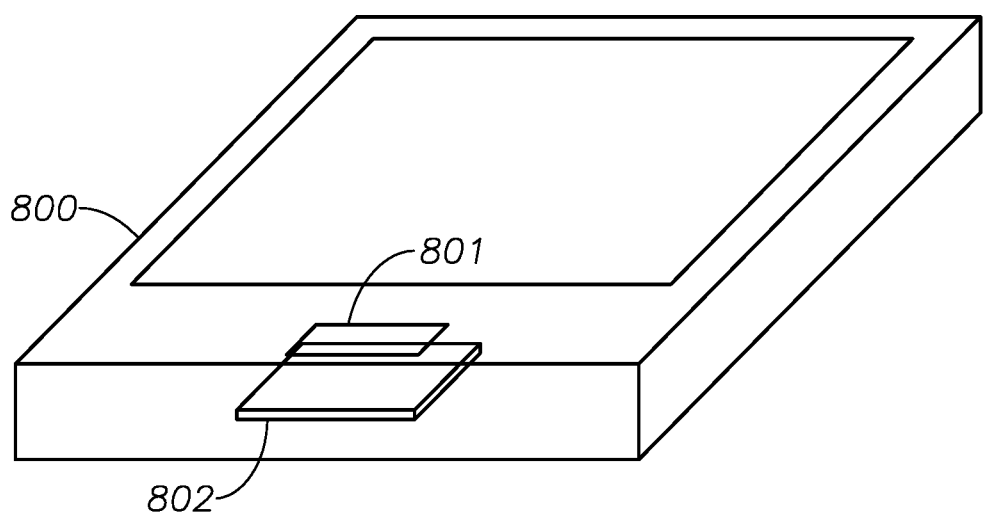
FIG. 8 is a schematic diagram of a case where a sensor array unit is incorporated in a mobile phone as an example of using the odor detection system according to an embodiment.

FIG. 8 is a schematic diagram of a portable device in which the sensor array unit according to an embodiment is incorporated.

According to at least one embodiment, the position to which the sensor array is incorporated can be set arbitrary; in FIG. 8, as an example, a sensor array unit 802 is provided just below a duct 801 of a microphone mounting portion of a smartphone 800 (just below a home button or just below a microphone component). In this configuration, a health check function which can detect oral troubles caused, for example, by periodontal disease or visceral disease can be provided.

4b. Wearable Device Provided with Odor Detection System

The system can be incorporated in a compact device. Thus, for example, the system or device can be mounted in a wearable device that is currently available in the market so that the obtained product can be used as an odor sensor. For example, if the system device is mounted on eye glasses, the obtained product can be used in various usages not limited to "e-nose."

4c. Utilization in Air Purifier, Ventilation, or Air Conditioner

When the system according to an embodiment is used in an air conditioner or the like, a process of measuring and identifying an odor factor in the room and then purifying air as necessary can be performed, and thus higher-quality function can be provided.

4d. Application to Medical Usage such as Breath Diagnosis Device

In the current medical field, a technique of performing disease diagnosis using a specific substance included in breath as a marker has been developed. When the system according to an embodiment is used, it can be considered that diagnosis accuracy is improved even if the breath includes a plurality of markers or detection substances. When the present system is used as such a diagnostic usage, a medical instrument can be designed and produced and then the system according to an embodiment can be incorporated therein. Alternatively, the sensor array unit or the like is incorporated in a mobile phone or smartphone as described above, information acquired by the sensor array unit can be used for remote diagnosis, for example, in medical institutions by communication with a server.

An odor detection system according to various embodiments is provided which has features that, when a plurality of individual sensor elements each having a different functional film on the surface thereof are sequentially arranged and mounted according to a certain rule, the rule is recorded together with production information in an arbitrary place on the network, that the rule is changed and recorded for each product information configured from an arbitrary cluster, such as each product, each production batch, or each production plant, and that an odor is identified by collating the response pattern with respect to a specific odor with the arrangement pattern data of sensors read from an arbitrary place on the network.

The odor detection system, the odor identification method, and the odor identification device according to various embodiments can totally determine and identify even an odor factor which cannot be identified by a conventional odor sensor. Thus, even with a mixed state of an unspecified number of odor causative substances, the odor factor configured by the odor causative substances can be detected and identified. Accordingly, the various embodiments can be not only used as an odor sensor for various devices, but can also be applied to air purifiers, medical use and the like.

REFERENCE NUMERALS

100 Odor Identification System
110 Sample Information Acquisition Unit

111 Sample Acquisition Unit
112 Sensor Array Unit
113 Sensor Data Processing Unit
120 Communication Means
130 Information Processing Unit
131 Receiving Unit
132 Sensor Arrangement Information Storing Unit
133 Odor Factor Information Storing Unit
134 Pattern Identification Unit
135 Display Unit

What is claimed is:

1. An odor detection system, comprising:
a sensor unit comprising a plurality of sensors configured to interact with odor causative substances included in a sample, in which the arrangement of the plurality of sensors can be varied;
a sensor data processing unit configured to process a result of the interaction obtained from the sensor unit as an interaction pattern information of the sample, the interaction being an interaction between the odor causative substances and the sensors;
a sensor arrangement information unit configured to store an arrangement information of the plurality of sensors in the sensor unit; and
a pattern identification unit configured to identify an odor of the sample by referring to the interaction pattern information of the sample, an interaction pattern information of a known odor and the arrangement information of the plurality of sensors.

2. The odor detection system according to claim 1, wherein the plurality of sensors each have a functional film configured to adsorb the odor causative substances and wherein each of the plurality of the sensors have different functional films in the sensor unit; and
wherein the plurality of sensors are configured to detect the frequency change of the functional films caused by adsorption of the odor causative substances onto the functional films.

3. The odor detection system according to claim 2, wherein at least one of the functional films is oscillated at a frequency different from others.

4. The odor detection system according to claim 2, wherein at least one of the plurality of sensors has a resonance frequency different from others.

5. The odor detection system according to claim 4, wherein at least one of the functional films has a thickness different from others.

6. The odor detection system according to claim 4, wherein the sensors are sensors having quartz substrates, and
wherein at least one of the quartz substrates of the plurality of sensors has a thickness different from others.

7. The odor detection system according to claim 2, wherein a composition or a degree of chemical modification is inclined in the functional films.

8. An odor identification method, comprising:
providing interaction of a plurality of sensors with odor causative substances on a sensor unit comprising the plurality of sensors which are configured to interact with the odor causative substances included in a sample and in which the arrangement of the plurality of sensors can be varied;
processing a result of the interaction obtained from the sensor unit as an interaction pattern information of the sample, the interaction being an interaction between the odor causative substances and the sensors; and
identifying an odor of the sample by referring to the interaction pattern information of the sample, an interaction pattern information of a known odor and an arrangement information of the plurality of sensors.

9. An odor identification device, comprising:
a sensor unit comprising a plurality of sensors configured to interact with odor causative substances included in a sample, in which the arrangement of the plurality of sensors can be varied;
a sensor data processing unit configured to process a result of the interaction obtained from the sensor unit as an interaction pattern information of the sample, the interaction being an interaction between the odor causative substances and the sensors;
a sensor arrangement information unit configured to store an arrangement information of the plurality of sensors in the sensor unit; and
a pattern identification unit configured to identify an odor of the sample by referring to the interaction pattern information of the sample, an interaction pattern information of a known odor and the arrangement information of the plurality of sensors.

10. The odor identification device according to claim 9, wherein the odor identification device is a portable device.

11. The odor identification device according to claim 9, wherein the odor identification device is a wearable device.

12. The odor identification device according to claim 9, wherein the odor identification device is an air conditioner.

13. A non-transitory computer-readable medium storing a program, the program allowing a computer to function as:
a sensor data processing unit configured to process a result of the interaction obtained from a sensor unit comprising a plurality of sensors configured to interact with odor causative substances included in a sample as an interaction pattern information of the sample, the interaction being an interaction between the odor causative substances and the sensors, wherein the arrangement of the plurality of sensors can be varied in the sensor unit; and
a pattern identification unit configured to identify an odor of the sample by referring to the interaction pattern information of the sample, an interaction pattern information of a known odor and an arrangement information of the plurality of sensors.

* * * * *